US010111805B2

(12) United States Patent
Park et al.

(10) Patent No.: US 10,111,805 B2
(45) Date of Patent: Oct. 30, 2018

(54) FACIAL MASSAGER

(75) Inventors: Changman Park, Seoul (KR);
Changkeun Lee, Seoul (KR); Taehong Shin, Seoul (KR); Seunghwan Yi, Seoul (KR); Cheonghwan Hwang, Seoul (KR); Wooram Park, Seoul (KR); Taekjin Oh, Seoul (KR); Byungyoung Kang, Seoul (KR); Myeong Hun Yeom, Seoul (KR); Gayoung Cho, Seoul (KR)

(73) Assignee: AMOREPACIFIC CORPORATION, Seoul (KR)

( * ) Notice: Subject to any disclaimer, the term of this patent is extended or adjusted under 35 U.S.C. 154(b) by 1284 days.

(21) Appl. No.: 14/239,057

(22) PCT Filed: Aug. 13, 2012

(86) PCT No.: PCT/KR2012/006434
§ 371 (c)(1),
(2), (4) Date: Aug. 11, 2014

(87) PCT Pub. No.: WO2013/027954
PCT Pub. Date: Feb. 28, 2013

(65) Prior Publication Data
US 2014/0350442 A1    Nov. 27, 2014

(30) Foreign Application Priority Data
Aug. 19, 2011    (KR) .................. 20-2011-0007512

(51) Int. Cl.
*A61H 23/02* (2006.01)
*A61N 1/30* (2006.01)
(Continued)

(52) U.S. Cl.
CPC ....... *A61H 23/0254* (2013.01); *A61H 39/002* (2013.01); *A61N 1/0428* (2013.01);
(Continued)

(58) Field of Classification Search
CPC .............. A61H 23/02; A61H 23/0254; A61H 2201/0157; A61H 2201/10;
(Continued)

(56) References Cited

U.S. PATENT DOCUMENTS 3,557,781 A    1/1971    Kaye, Sr.
4,052,981 A   10/1977    Bachmann
(Continued)

FOREIGN PATENT DOCUMENTS

JP    6004846 Y2    2/1994
JP    H10898863 A   4/1996
(Continued)

OTHER PUBLICATIONS

International Search Report of PCT/KR2012/006434 dated Feb. 15, 2013.

*Primary Examiner* — Colin W Stuart
*Assistant Examiner* — Douglas Sul
(74) *Attorney, Agent, or Firm* — Heedong Chae; Lucem, PC

(57) ABSTRACT

A device for face for forming a relatively high potential difference between power terminals of different polarities without a voltage booster circuit to make a lot of current flow through human skin such that function of iontophoresis may be remarkably improved and simultaneously for driving electrically-driven modules of a mask individually without an external power supply to stimulate entirely or partially. The massage device for face includes a mask including an accommodation formed therein and a terminal exposing hole of a terminal for making current to human skin, and at least one electrically-driven module accommodated in the accommodation of the mask, exposing two terminals of different polarities to the outside through the terminal exposing hole, a driving unit having a rotary shaft and a coil wrapping the (Continued)

rotary shaft, and increasing a potential difference between the two terminals using an induced electromotive force of the coil.

4 Claims, 11 Drawing Sheets

(51) Int. Cl.
*A61N 1/04* (2006.01)
*A61N 1/32* (2006.01)
*A61H 39/00* (2006.01)
*A61N 1/36* (2006.01)

(52) U.S. Cl.
CPC ........... *A61N 1/0484* (2013.01); *A61N 1/303* (2013.01); *A61N 1/322* (2013.01); *A61N 1/36014* (2013.01); *A61H 2201/165* (2013.01); *A61H 2201/5002* (2013.01); *A61H 2205/022* (2013.01)

(58) Field of Classification Search
CPC .......... A61H 2201/5005; A61H 39/002; A61H 2205/022; A61N 1/0484; A61N 1/325
See application file for complete search history.

(56) References Cited

U.S. PATENT DOCUMENTS

| | | | |
|---|---|---|---|
| 5,036,422 A * | 7/1991 | Uchida | H01H 47/22 361/159 |
| 5,072,724 A * | 12/1991 | Marcus | A61H 23/0245 601/148 |
| 5,099,829 A | 3/1992 | Wu | |
| 5,583,478 A | 12/1996 | Renzi | |
| 5,717,303 A * | 2/1998 | Engel | B60L 7/003 307/56 |
| 5,782,779 A | 7/1998 | Kilgore | |
| 7,127,285 B2 * | 10/2006 | Henley | A61N 1/044 604/20 |
| 7,182,739 B2 | 2/2007 | Kopanic | |
| 7,349,733 B2 * | 3/2008 | Joshi | A61N 1/0428 604/20 |
| 7,630,203 B1 | 12/2009 | Chen | |
| 2004/0220622 A1 * | 11/2004 | Bernabei | A61H 7/008 607/3 |
| 2006/0030749 A1 | 2/2006 | Hung | |
| 2006/0178602 A1 | 8/2006 | Teng | |
| 2006/0200052 A1 | 9/2006 | Lin | |
| 2006/0258963 A1 | 11/2006 | Kopanic, Jr. | |
| 2007/0179414 A1 | 8/2007 | Imboden | |
| 2007/0277835 A1 | 12/2007 | Ariav | |
| 2008/0027363 A1 | 1/2008 | Brueckmann | |
| 2008/0208085 A1 | 8/2008 | Nan | |
| 2008/0228114 A1 | 9/2008 | Nan | |
| 2009/0017778 A1 | 1/2009 | Akieda | |
| 2009/0062700 A1 | 3/2009 | Lin | |
| 2009/0086447 A1 | 4/2009 | Sugimoto | |
| 2010/0010292 A1 | 1/2010 | Talbot | |
| 2010/0174217 A1 | 7/2010 | Budnik | |
| 2010/0236130 A1 | 9/2010 | Basso | |
| 2010/0268021 A1 | 10/2010 | Standfest | |
| 2011/0092863 A1 | 4/2011 | Kim | |
| 2011/0224754 A1 | 9/2011 | Wei | |
| 2012/0022411 A1 * | 1/2012 | Wu | A61H 23/02 601/15 |
| 2012/0023785 A1 | 2/2012 | Barnes | |
| 2012/0116273 A1 | 5/2012 | Nan | |
| 2012/0184884 A1 | 7/2012 | Dyer | |
| 2012/0245439 A1 | 9/2012 | Andre | |
| 2013/0041211 A1 | 2/2013 | Zamar | |

FOREIGN PATENT DOCUMENTS

| | | | |
|---|---|---|---|
| JP | 3137239 U | 10/2007 | |
| KR | 20-0219490 Y1 | 4/2001 | |
| KR | 20-0276414 Y1 | 5/2002 | |
| KR | 10-2008-0023714 A | 3/2008 | |
| KR | 10-2009-0121643 A | 11/2009 | |
| KR | 10-2011-0054997 A | 5/2011 | |
| WO | WO 2010007565 A2 * | 1/2010 | ........... A61K 9/0009 |

* cited by examiner

FACIAL MASSAGER

CROSS REFERENCE RELATED APPLICATION

This application claims foreign priority of Korean Patent Application No. 20-2011-0007512, filed on Aug. 19, 2011, which is incorporated by reference in its entirety into this application.

BACKGROUND OF THE INVENTION

1. Field of the Invention

The present invention relates to a facial massage device, and more particularly to a massage device for face for forming a relatively high potential difference between power terminals of different polarities without a voltage booster circuit to make a lot of current flow through human skin such that function of iontophoresis may be remarkably improved and at the same time for driving electrically-driven modules of a mask individually without an external power supply to stimulate whole or a part of face.

2. Description of the Prior Art

In general, for the improved elasticity and anti-aging of skin, functional cosmetics such as various kinds of cosmetics and massage creams are used while professional massage shops, which manage costumers' skin using these cosmetics, are thriving.

Moreover, a massage device (hereinafter, referred to as a "facial massage device") stimulating human face is provided and is configured to attach a vibration motor to a face-shaped mask to apply vibration to the human face such that blood can be easily circulated and skin aging can be delayed.

FIG. 1 is a view illustrating an existing facial massage device. As illustrated, the existing massage device for face includes a galvanic ion current generator 10, a working electrode 11 provided in the galvanic ion current generator 10, a coupling device 20 for working electrode connected to the working electrode 11 in parallel, an opposite electrode 12 attached to a desired spot of user's face, a face contact unit 30 for an opposite electrode connected to the opposite electrode 12, and a wet matrix skin pack 40.

However, since the existing massage device for face is operated such that the wet matrix skin pack and the galvanic ion current generator are electrically connected to the coupling device for the working electrode and that galvanic ion current is applied from the galvanic ion current generator to the wet matrix skin pack, the existing massage device for face is operable only when to have the coupling device for an working electrode and the coupling device and a user can be serviced with massage function by ion current only when the existing massage device for face must have the wet matrix skin pack and the galvanic ion current generator.

Iontophoresis is a method of increasing permeation of ionic medicine through human skin by forming a potential difference on human skin and changing electric circumstance of skin and has an important key of forming maximum current. That is, skin resistance of human body is very high, from several tens kΩ to several tens MΩ, so that a relatively high input voltage is required to introduce a sufficient current into skin. Due to these reasons, the existing massage device for face using the iontophoresis usually includes a voltage booster circuit in an ion current generator, so that the ion current generator is complicated in structure, that overall size of the existing massage device for face increases, and that it is inconvenient to carry and keep in custody.

In addition, since, in the existing facial massage device, the ion current is supplied from the galvanic ion current generator to the whole wet matrix skin pack, a user cannot be serviced with the iontophoresis stimulation function only to a specific portion of face as occasion demands or vice versa. For example, a user cannot be serviced with the stimulation function even when the user has a wound on his/her face and wishes to be serviced with the stimulation function only to other portions of face except for the wound. Thus, a user should abandon use of the existing massage device for face or be serviced with the face massage function while bearing pain of the wound.

SUMMARY OF THE INVENTION

Accordingly, the present invention has been made to solve the above-mentioned problems occurring in the prior art, and an object of the present invention is to provide a massage device for face including a plurality of electrically-driven modules for forming a relatively high potential difference between power terminals of different polarities using induced electromotive force by inertial rotation without a voltage booster circuit to make a lot of current flow through human skin such that effect of iontophoresis may be maximized.

The present invention also provides a massage device for face driven by a mask itself without an external power supply to provide skin stimulation and a massage function accompanying iontophoresis.

The present invention also provides a massage device for face for providing skin stimulation and a massage function accompanying iontophoresis only to a specific portion of user's face, on the contrary to the remaining portion of the user's face except for the specific portion, and enabling a user to select the skin stimulation accompanying iontophoresis and a portion to be massaged.

In order to accomplish this object, there is provided a massage device for face including: a mask including an accommodation formed therein and a terminal exposing hole of a terminal for making current to human skin; and at least one electrically-driven module accommodated in the accommodation of the mask, exposing two terminals of different polarities to the outside through the terminal exposing hole, a driving unit having a rotary shaft and a coil wrapping the rotary shaft, and increasing a potential difference between the two terminals using an induced electromotive force of the coil.

Moreover, the mask includes a first mask and a second mask circumferences of which are fixed to each other to form the accommodation, and at least one of the first mask and the second mask include at least one of an insertion hole for inserting and withdrawing the electrically-driven module.

The electrically-driven module includes: a base including power terminals of different polarities formed on a side to drive the a vibrator and connected to each other through human skin as a conductor; the (a) vibrator installed on at least one side of the base; the driving unit installed in the base and including the rotary shaft for providing a driving force to the vibrator and the coil interposing the rotary shaft therein; a driving switch installed at a power input end of the driving unit to switch on/off a power supply of the driving unit; a controller controlling the switching on/off of the driving switch to control operating state of the driving unit and vibration state of the vibrator according to the operation of the driving unit; an induced electromotive force processor including an input end connected between the driving switch and the driving unit in parallel and making electric energy generated from the coil around the rotary shaft when the driving is idle by the switching off of the driving switch flow to an output end of the driving unit.

The controller controls the driving switch to switch on/off by a preset time interval in pulse width modulation (PWM).

The massage device for face further includes a wearing unit enabling a user to wear the mask on his/her head.

According to an embodiment of the present invention, since a massage device for face includes a plurality of electrically-driven modules forming a relatively high potential difference between power terminals of different polarities using induced electromotive force by inertial rotation of a driving unit without a booster circuit, a lot of current may flow through human skin so that effect of the iontophoresis can be maximized and the skin stimulation and the massage function can be provided.

Moreover, the plurality of the electrical-driven modules of a mask, driven individually by own power supplies, is driven without an external power supply such that a user may be serviced with the skin stimulation and the massage function and that user convenience and mobility can be improved.

In addition, the massage device for face of the present invention provides the skin stimulation and the massage function accompanying iontophoresis only to a specific portion of a user's face, on the contrary to the remaining portion of the user's face except for the specific portion, and enables a user to select a portion to be serviced with the skin stimulation and/or the massage function accompanying iontophoresis by considering facial skin conditions of his/hers.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Hereinafter, a massage device for face according to a preferred embodiment of the present invention will be described with reference to the accompanying drawings.

Figure 1:
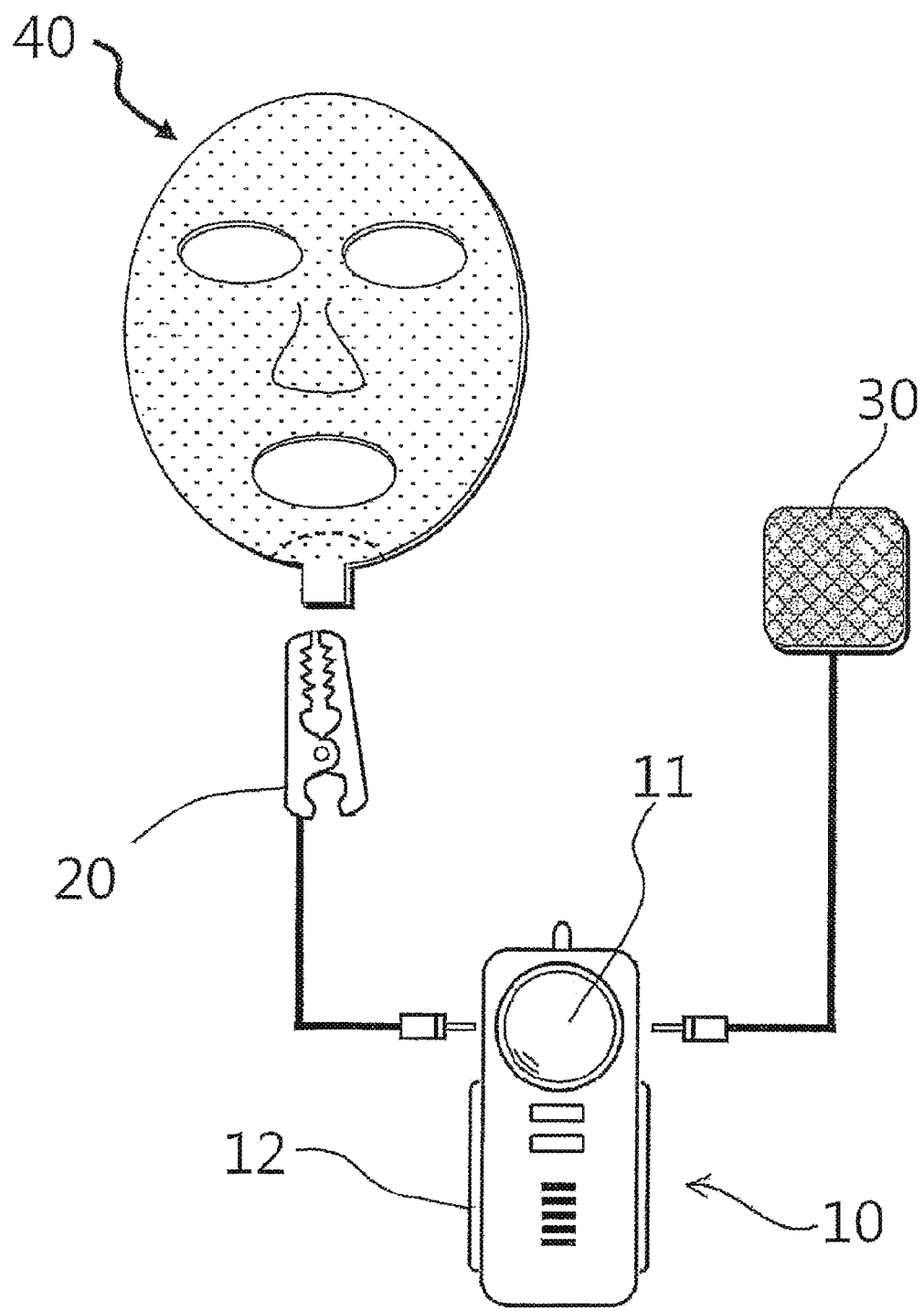
FIG. 1 is a view illustrating an existing facial massage device.
Figure 2:
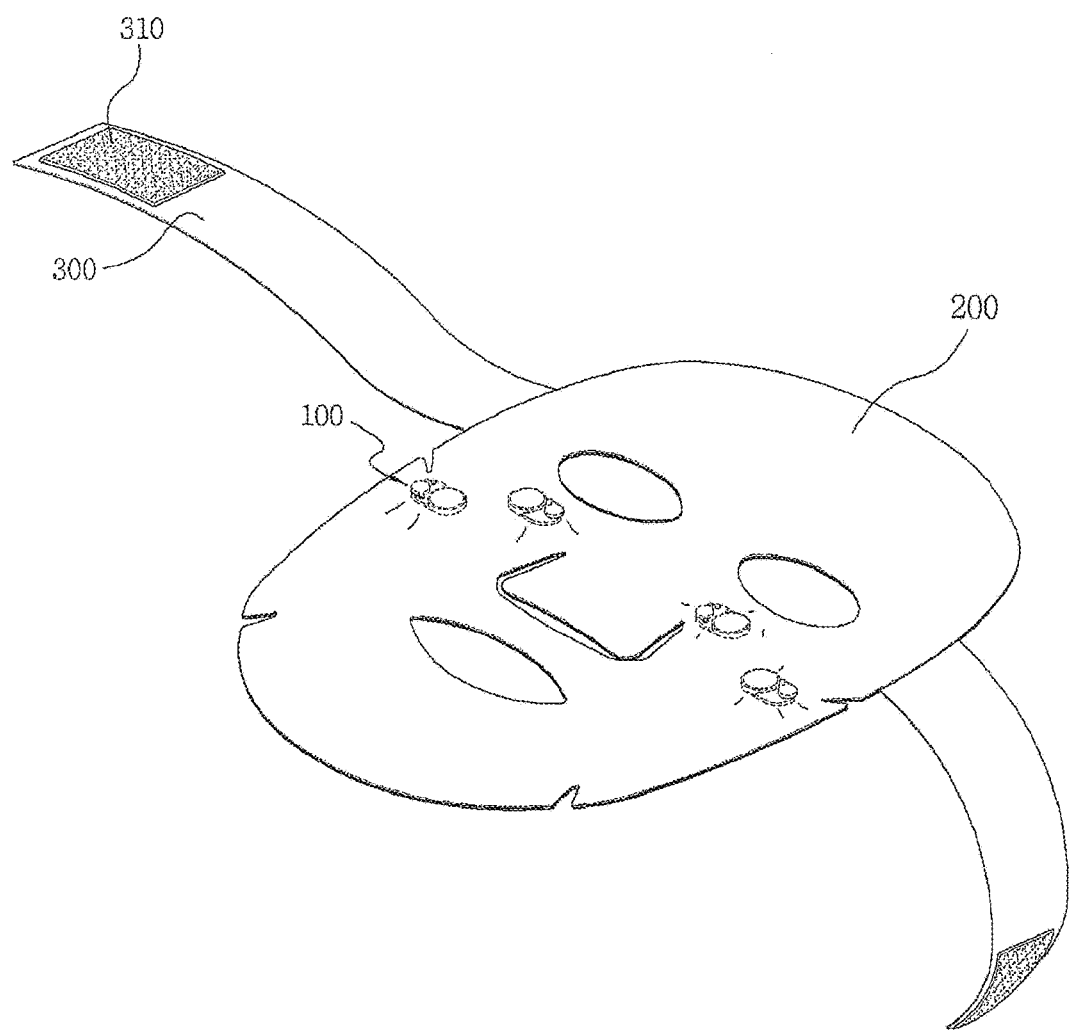
FIG. 2 is a perspective view illustrating a massage device for face according to an embodiment of the present invention.
Figure 3:
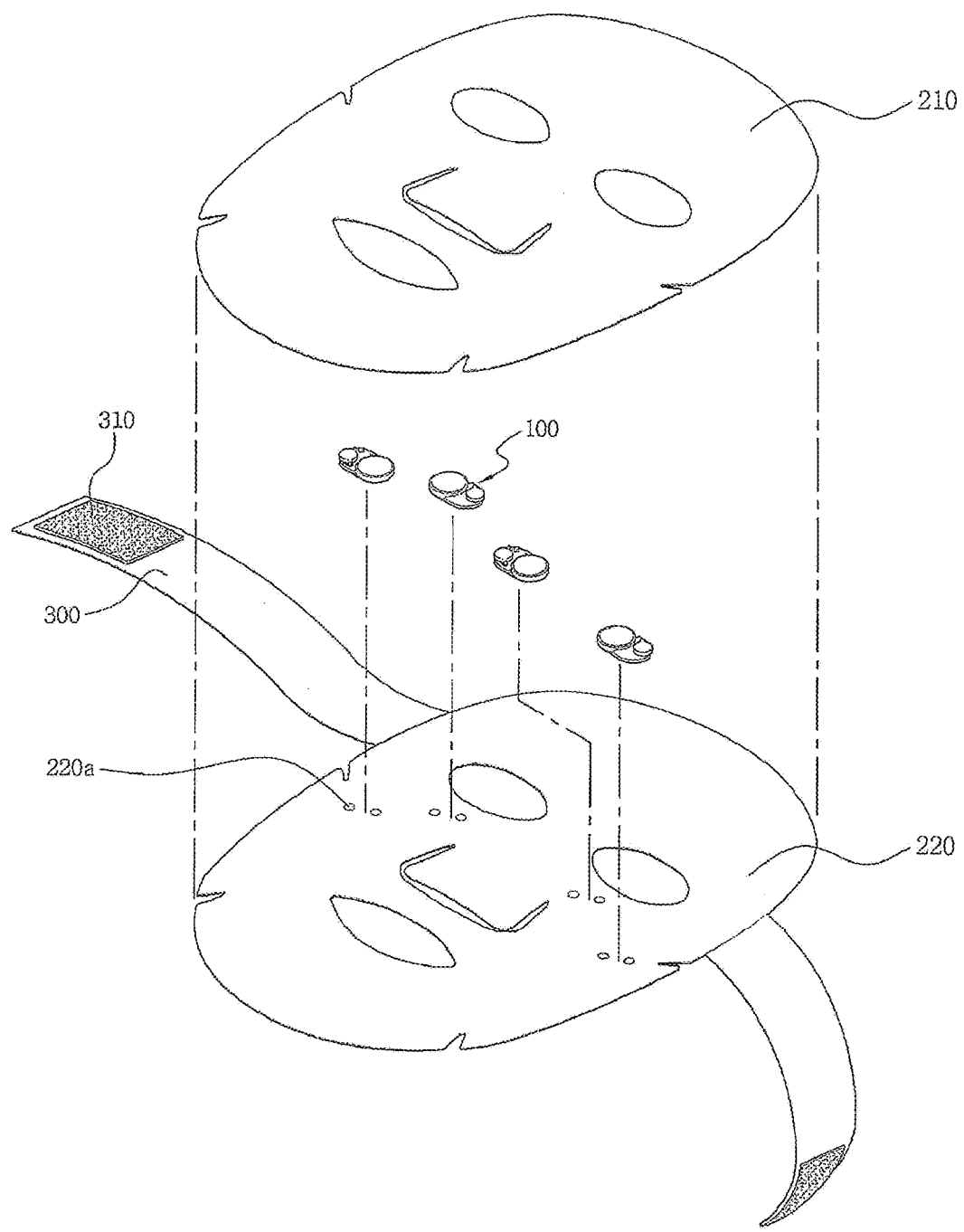
FIG. 3 is an exploded perspective view illustrating the massage device for face according to the embodiment of the present invention.
Figure 4:
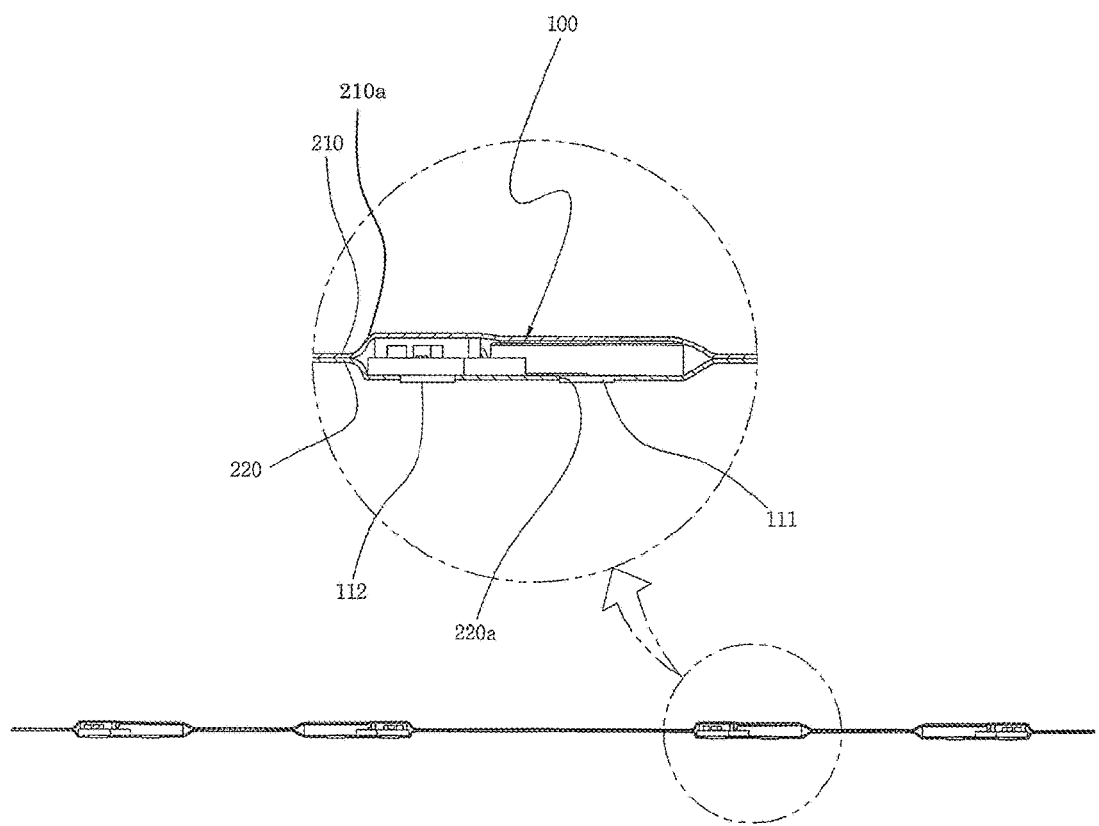
FIG. 4 is a sectional view taken along the line A-A of FIG. 3.
Figure 5:
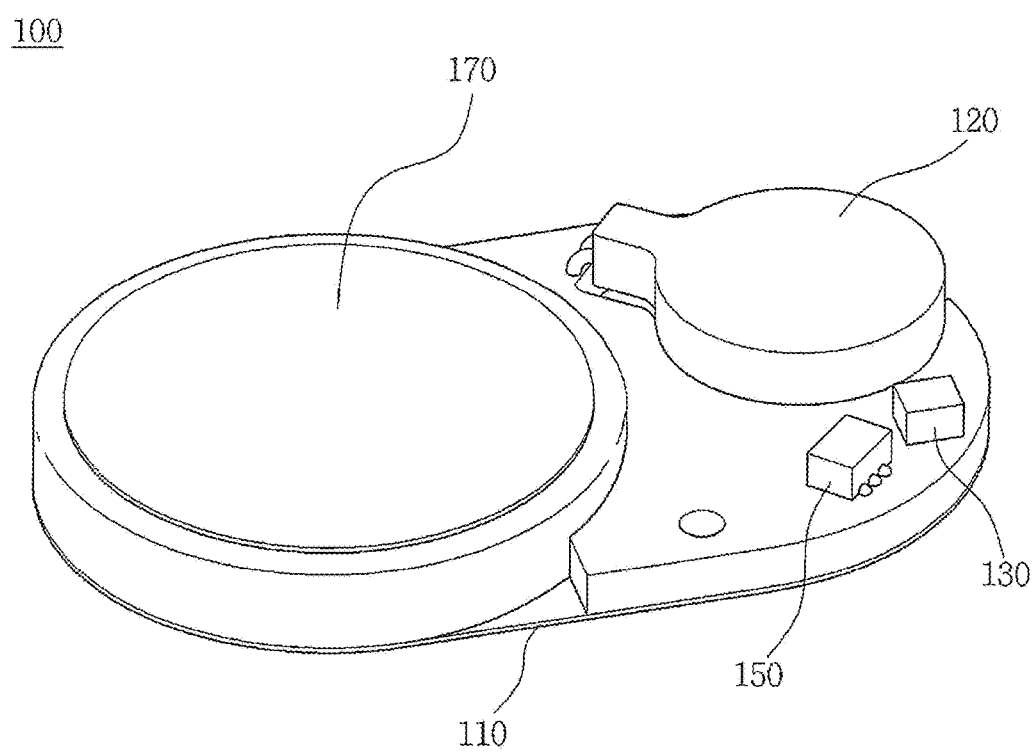
FIG. 5 is a perspective view illustrating an electrically-driven module of the massage device for face according to the embodiment of the present invention.
Figure 6:
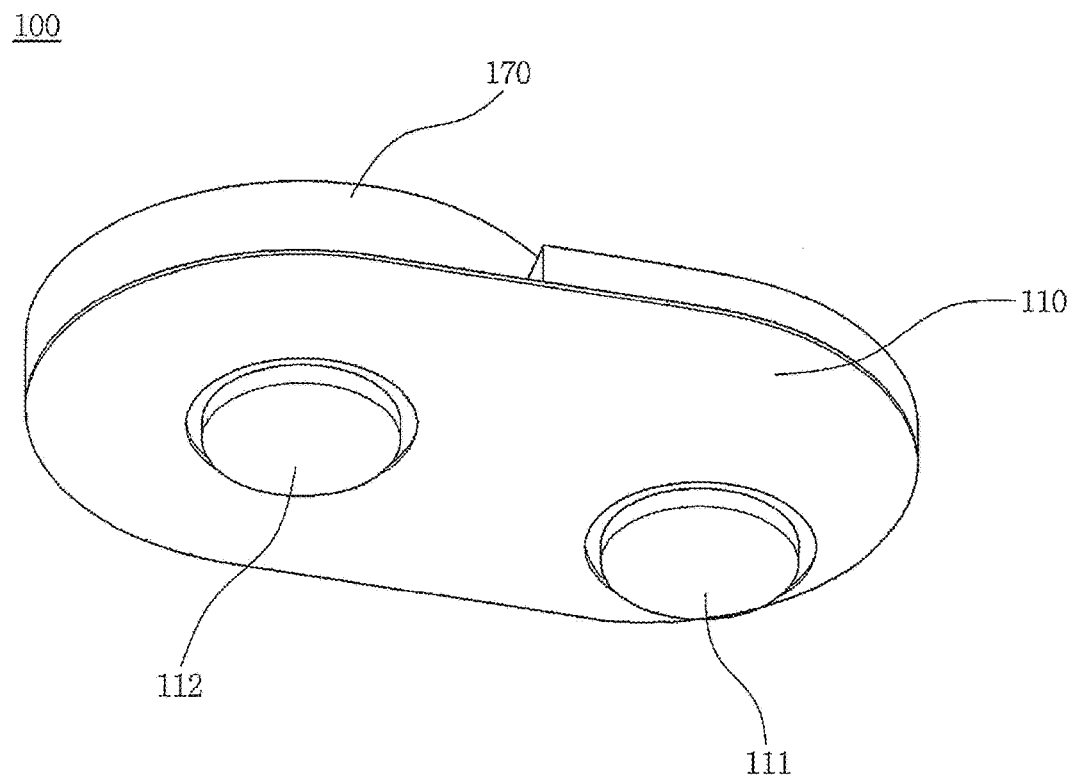
FIG. 6 is a rear perspective view illustrating a skin stimulation electrically-driven module of the massage device for face according to the embodiment of the present invention.
Figure 7:
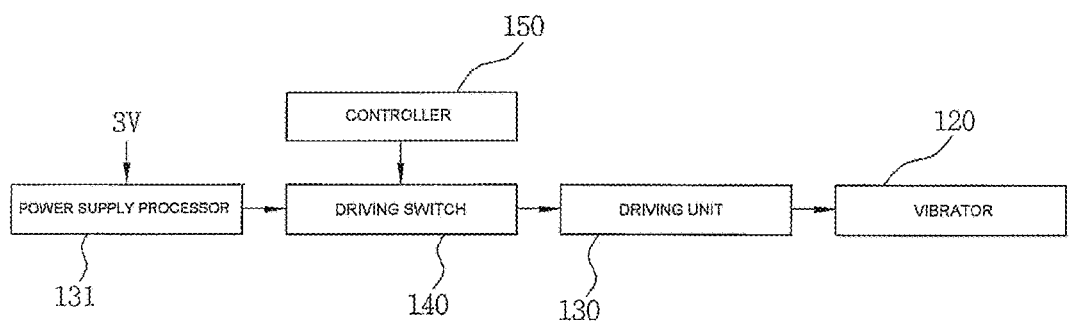
FIG. 7 is a block diagram illustrating the skin stimulation electrically-driven module of the massage device for face according to the embodiment of the present invention.
Figure 8:
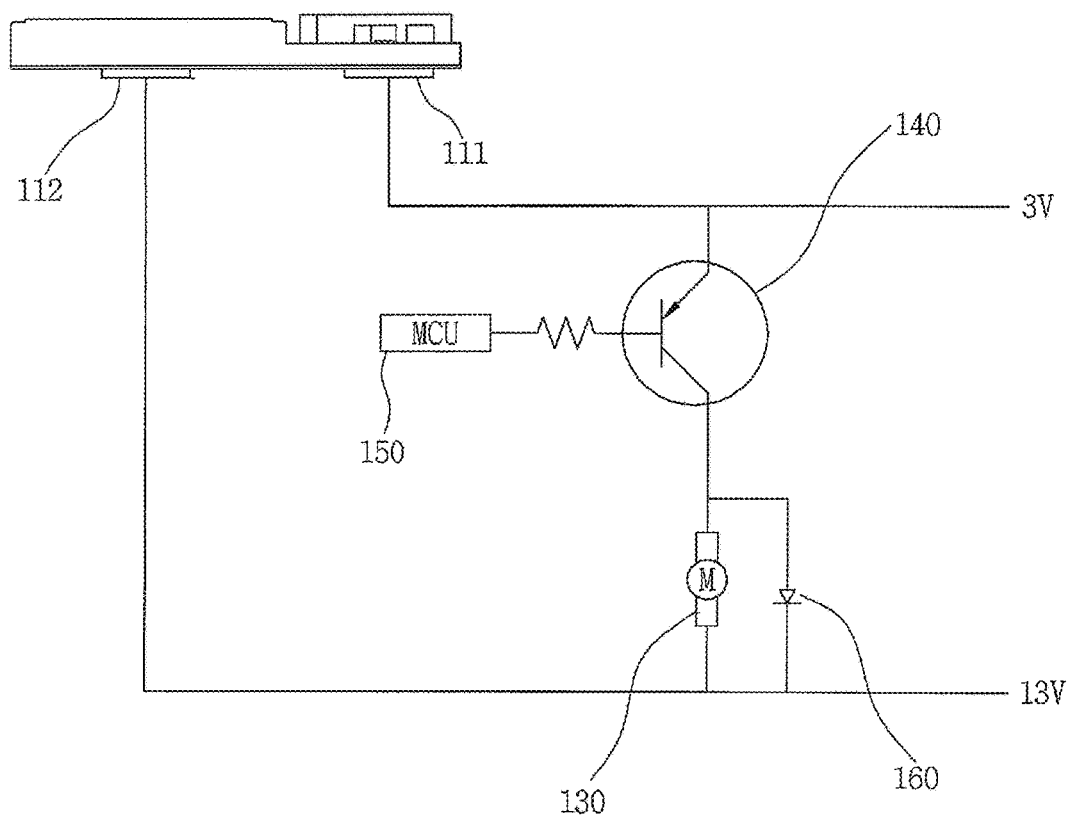
FIG. 8 is a view schematically illustrating a circuit through which induced electromotive force of the skin stimulation electrically-driven module of the massage device for face according to the embodiment of the present invention.

FIG. 2 is a perspective view illustrating a massage device for face according to an embodiment of the present invention. FIG. 3 is an exploded perspective view illustrating the massage device for face according to the embodiment of the present invention. FIG. 4 is a sectional view taken along the line A-A of FIG. 3.

As illustrated, the massage device for face according to the embodiment of the present invention includes a mask and a plurality of electrically-driven modules.

First, referring to FIG. 2, schematic structure and operations of the massage device for face according to the embodiment of the present invention will be described.

A mask 200 has an accommodation for accommodating an electrically-driven module 100 and the electrically-driven module 100 is accommodated in the accommodation of the mask to provide skin stimulation and a massage function accompanying iontophoresis through outputting its vibration and current to human skin. At least one of the electrically-driven module 100 may be provided wherein the electrically-driven module 100 includes own power supply and is capable of being driven individually. Thus, the massage device for face of this embodiment drives the electrically-driven module 100 of the mask 200 such that the massage function may be provided and a specific portion of human face or the remaining portion except for the specific portion may be serviced with massage.

Next, the detailed structure of the massage device for face according to the embodiment of the present invention will be described with reference to FIGS. 2 to 4.

Referring to FIGS. 2 to 4, the massage device for face includes a first mask 210, a second mask 220, and the electrically-driven module 100. The massage device for face may further include a wearing unit 300.

Circumferences of the first mask 210 and the second mask 220 are fixed to each other to form the accommodation inside them. At least one of the first mask 210 and the second mask 220 includes an insertion hole 210a formed to insert or withdraw the electrically-driven module 100 or an insulator 180 of the electrically-driven module 100. In this embodiment, the first mask 210 has the insertion hole 210a to withdraw the insulator 180 out of the accommodation. Moreover, at least one of the first mask 210 and the second mask 220 includes a terminal exposing hole 220a to expose power terminals 111 and 112 of different polarities of the electrically-driven module 100. In this embodiment, the second mask 220 has the terminal exposing hole 220a.

The electrically-driven module 100 will be described with reference to FIGS. 5 to 11. Referring to FIGS. 5 to 11, the electrically-driven module 100 includes a base 110, a vibrator 120, a driving unit 130, a driving switch 140, a controller 150, and an induced electromotive force processor 160. The electrically-driven module 100 may further include a battery 170.

The base 110 includes the power terminals 111 and 112 of different polarities formed on a side thereof to drive the vibrator 120. In this case, the power terminals 111 and 112 supply electric power to the driving unit 130 driving the vibrator 120, so that the vibrator 120 is vibrated by the driving unit 130. Moreover, the power terminals 111 and 112 are connected to each other through human skin as a conductor and this is for iontophoresis of forming a potential difference on the human skin to change electric circumstance of the human skin and by increasing permeation of ionic medicine.

The vibrator 120 is installed on at least one side of the base 110 and vibrates in a preset pattern according to operation of the later-described driving unit 130. Vibrations of the vibrator 120 are transmitted to the base 110 so that whole the base 110 vibrates when the vibrator 120 vibrates.

The driving unit 130 is installed in the base 110 and includes a rotary shaft (not shown) providing driving force to the vibrator 120 and a coil interposing the rotary shaft therein. A DC motor is a typical example of the driving unit 130. Thus, although hereinafter the driving unit 130 will be described by a DC motor, the present invention is not limited thereto. A reference numeral 131 indicates a power supply processor installed in a power input end of the driving unit 130.

The driving switch 140 is installed at a power input end of the driving unit 130 and switches on/off to supply electric power to the driving unit 130 or to interrupt the electric power supplying to the driving unit 130. In this embodiment, the driving switch 140 is a transistor an emitter of which is supplied with a driving power, a base of which is supplied with a pulse signal from the controller 150. The present invention is not limited thereto, but the driving switch 140 may be various types satisfying conditions that a switch is on/off by a pulse signal to supply electric power to or interrupt power supplied to the driving unit 130. Moreover, in this embodiment the driving power supplied to the driving unit 130 is 3 V.

The controller 150 controls ON/OFF of the driving switch 140 such that operating state of the driving unit 130 and vibration state of the vibrator 120 according to the operation of the driving unit 130 are controlled. The controller 150 controls the driving unit 130 in Pulse Width Modulation (PWM). That is, when a pulse signal of the controller 150 is applied to the base of the transistor, that is, the driving switch 140, the transistor repeats ON/OFF by preset time interval according to the pulse signal.

The induced electromotive force processor 160 includes an input end connected between the driving switch 140 and the driving unit 130 in parallel and an output end connected to an output end of the driving unit 1390 in parallel. The induced electromotive force processor 160 makes electric energy, which is generated by a coil around the rotary shaft of the driving unit 130, flow to the output end of the driving unit 130 when the driving unit 130 is idle by OFF operation of the driving switch 140. That is, a DC motor as the driving unit 130 is driven when electric power is supplied by switching on of the driving switch 140 and still rotates due to the rotational inertia even when the driving switch 140 is switched off according to a pulse signal, while an induced electromotive force is generated at the coil of the DC motor.

The induced electromotive force generated at the coil of the DC motor is applied to an output end of the driving unit (DC motor) 130, and thus is applied to a minus (−) power terminal of the base 110 electrically connected to the output end of the driving unit 130 so that a relatively lot of current flows. In other words, a driving power of 3 V is applied to the DC motor as the driving unit 130, that is, a voltage of a plus (+) power terminal of the base 110 is 3 V while a voltage of the minus power terminal of the base 110 becomes 13 V by the induced electromotive force applied from the coil of the DC motor.

The battery 170 supplied electric power to the electrically-driven module 100.

Moreover, in this embodiment, although the induced electromotive force processor 160 is a power diode, the present invention is not limited thereto but the induced electromotive force processor 160 may be various types satisfying conditions that the induced electromotive force generated at the coil of the DC motor is applied to the output end of the DC motor.

In this embodiment, the base 110 is a printed circuit board on which the driving unit 130, the driving switch 140, the controller 150, and the induced electromotive force processor 160 are mounted and includes circuit patterns for the electric connection between the mounted components. The printed circuit board may be a flexible printed circuit board (FPCB) and this is to make the base 110 be easily attached to human skin along the contour of the human skin and vibration of the vibrator 120 be transmitted to the human skin more effectively.

Due to the above-mentioned structure, the electrically-driven module 100 increases potential difference between the power terminals 111 and 112 of different polarities using the induced electromotive force generated at the coil of the DC motor without a voltage booster circuit so that more amount of current may flow through the human skin and that effect of the iontophoresis may be also improved.

Moreover, since the boosting of the power terminals 111 and 112 directly making a contact with the human skin is performed using current of the induced electromotive force generated from the coil of the rotary shaft without a voltage booster circuit nor consumption of the battery 170, consumption of the battery 170 can be minimized.

Moreover, since vibration is transmitted to the human skin through the entire skin stimulation electrically-driven module 100, a vibration transmission region extends and a relatively complicated voltage booster circuit is not needed so that overall volume of the skin stimulation electrically-driven module 100 is decreased and its mobility is improved.

Figure 9:
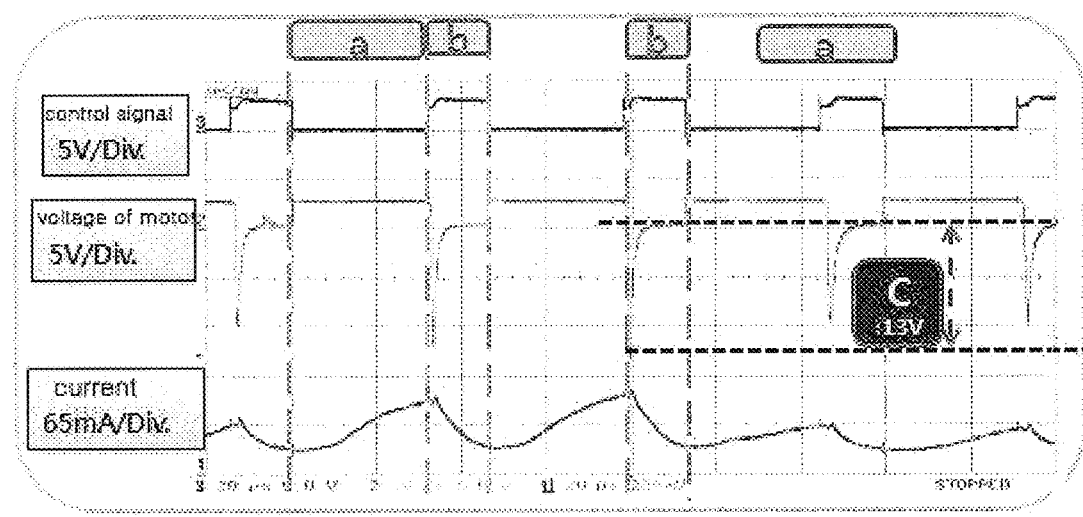
FIGS. 9 and 10 are graphs showing variation of an output voltage from the skin stimulation electrically-driven module of a driving unit of the massage device for face according to the embodiment of the present invention.
Figure 10:
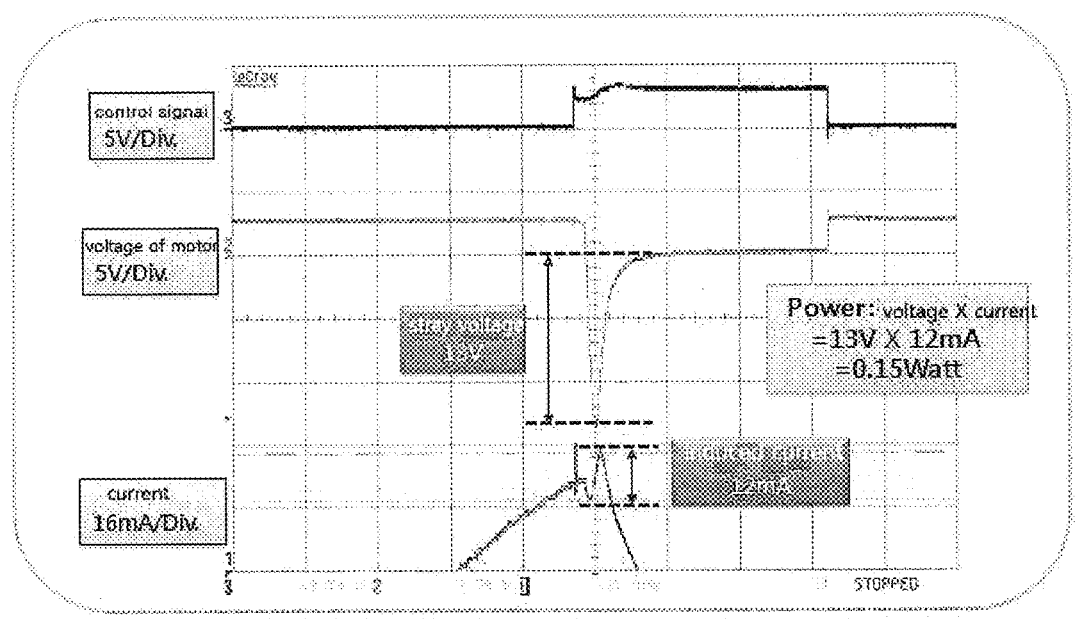

FIGS. 9 and 10 are graphs showing variation of an output voltage from the skin stimulation electrically-driven module of a driving unit of the massage device for face according to the embodiment of the present invention.

Referring to FIG. 9, an electric power is supplied to the DC motor in a zone "a" and the electric power is not supplied to the DC motor in a zone "b". In this embodiment, a voltage of 5 V is applied to the input end of the DC motor so that a pulse signal of 5 V is applied from the controller 150 to the driving switch 140. A zone "c" indicates voltages of the induced electromotive force generated at the zone "b". As illustrated, the induced electromotive force of maximum 13 V is generated at the zone where an electric power is not supplied to the DC motor.

As illustrated in FIG. 10, as the induced electromotive force of maximum 13 V is generated at the zone "b", it is confirmed that a current of maximum 12 mA flows through the human skin. In this case, the induced electromotive force and operation of the current to the human skin are applied in the form of discontinuous impulses and these operations are similar as acupuncture on the human skin, so that the human skin may be received with useful stimulation and that massage and treatment effect may be also provided.

Referring to FIGS. 2 to 4 again, the wearing unit 300 enables a user to wear the mask on his/her head (face). Although the wearing unit 300 assumes the form of a hair band in this embodiment, the present invention is not limited thereto. The wearing unit 300 includes a pair of bands one ends of which are fixed to the lateral sides of the mask 200 and in which Velcro tapes 310 are attached to the other ends thereof for the coupling between the bands. When the Velcro tapes 310 are relatively elongated, a user adjusts contact portions between the Velcro tapes 130 so that a length of the band type wearing unit 300 may be adjusted.

As seen from the embodiment of FIGS. 2 to 10, since the electrically-driven module forms a relatively high potential difference between power terminals of different polarities using the induced electromotive force by inertial rotation of the driving unit without a voltage booster circuit, the massage device for face according to the embodiment of the present invention makes a lot of current flow through the human skin so that effect of the iontophoresis may be maximized and that the skin stimulation and a massage function may be provided.

Moreover, the plurality of the electrically-driven (vibration) modules of a mask, driven individually by own power supplies, is driven without an external power supply such that a user may be serviced with the skin stimulation and the massage function and that user convenience and mobility can be improved.

In addition, the massage device for face of the present invention provides the skin stimulation and the massage function accompanying iontophoresis only to a specific portion of a user's face, on the contrary to the remaining portion of the user's face except for the specific portion, and enables a user to select a portion to be serviced with the skin stimulation and/or the massage function accompanying iontophoresis by considering facial skin conditions of his/hers.

Figure 11:
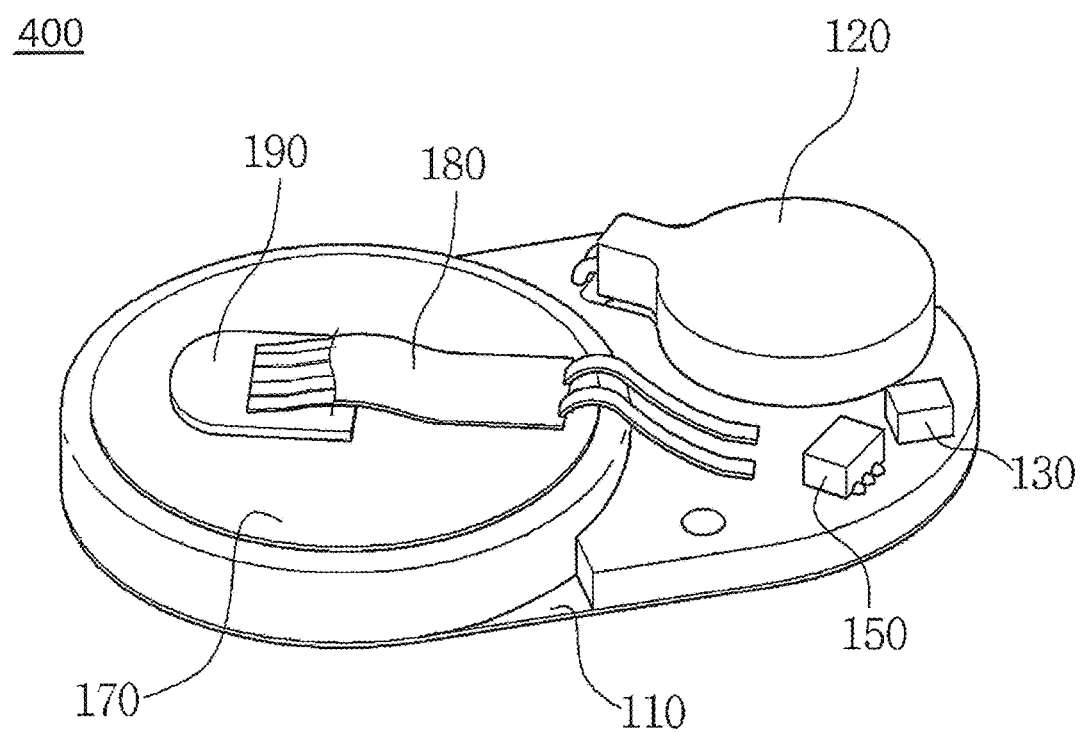
FIG. 11 is a perspective view illustrating a skin stimulation electrically-driven module of a massage device for face according to another embodiment of the present invention.

Meanwhile, FIG. 11 is a perspective view illustrating a skin stimulation electrically-driven module of a massage device for face according to another embodiment of the present invention. As illustrated, each of the electrically-driven module 400 includes a power connection member 180 and an insulator 190. The remaining components of the electrically-driven module 400 are identical to the electrically-driven module 100 according to the embodiment as illustrated in FIGS. 2 to 10 and thus their detailed descriptions will be omitted but same reference numerals are still used.

The battery 170 is installed in the base 110 and supplies electric power to the driving unit 130 and the controller 150 through the power connection member 180.

The power connection member 180 electrically connects power terminals (not shown) of the battery 170 to power terminals (not shown) of the driving unit 130 formed on the base 110. In other words, the driving unit 130 is electrically connected to the battery 170 through the power connection member 180. The power terminals of the base 110 may supply electric power to the controller 150, so that the base 110 includes circuit patterns connecting the power terminals to the driving unit 130 and the controller 150 in parallel.

The insulator 190 is attached to a contact area between the power terminals and the power connection member 180. That is, the insulator 190 is attached to the battery 170 to interrupt the electric connection between the power terminals of the battery 170 and the power connection member 180 and the electric connection between the power terminals of the battery 170 and the power connection member 180 is completed when the insulator 190 is removed from the battery 170. In this case, the insulator 190 is detachably attached to the battery 170 and the electric connection between the power terminals of the battery 170 and the power connection member 180 is controlled by the attachment and detachment of the insulator 190 to supply and interrupt the electric power to the driving unit 130.

That is, the insulator 190 may switch between the power terminals and the power connection member 180, while the skin stimulation electrically-driven module 400 may be configured such that the electric power of the battery 170 can be consumed only when to use by the switching function of the insulator 190 without a switch. In other words, the removal of a switch makes the skin stimulation electrically-driven module 400 be reduced in volume and the consumption of the battery 170 may be performed only when the vibrator 120 is driven.

Although in this embodiment the insulator 190 is a attachable thin seat to screen the power terminals of the battery 170, the present invention is not limited thereto but the insulator 190 may be changed and modified into various types under the conditions where the insulator 190 is detachably attached to the power terminal region of the battery 170 and supplies electric power between the power terminals of the battery 170 and the power connection member 180. The insulator 190, although not depicted in the drawings, may include an extension exposed to the outside of the mask 200 such that a user may manipulate the insulator 190 with the extension.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A massage device for face comprising:
   a mask comprising:
      an accommodation formed therein;
      a terminal exposing hole of a terminal; and
      a first mask and a second mask, wherein a circumference of the first mask and a circumference of the second mask are fixed to each other to form the accommodation; and
   at least one electrically-driven module, accommodated in the accommodation of the mask, comprising:
      a driving unit having a rotary shaft and a coil wrapping the rotary shaft; and
      a battery,
   wherein the electrically-driven module exposes two terminals of different polarities to an outside of the mask through the terminal exposing hole and increases a potential difference between the two terminals using an induced electromotive force of the coil,
   wherein at least one of the first mask and the second mask comprises at least one of an insertion hole for inserting and withdrawing the electrically-driven module, and
   wherein an induced electromotive force processor comprises an input end connected between a driving switch and the driving unit in parallel and making electric energy generated from the coil around the rotary shaft when the driving unit is idle by the switching off of the driving switch flow to an output end of the driving unit,
   wherein a minus (−) power terminal of the base is electrically connected to the output end of the driving unit such that a current flows when the driving unit is idle by the switching off of the driving switch flow to an output end of the driving unit, and
   wherein the current is configured to flow between the power terminals through the user's skin.

2. The massage device for face as claimed in claim 1, wherein the electrically-driven module further comprises:

a base comprising power terminals of different polarities formed on a side to drive a vibrator and are configured to be connected to each other through the user's skin as a conductor;

the vibrator installed on at least one side of the base;

the driving unit installed in the base comprising the rotary shaft for providing a driving force to the vibrator and the coil interposing the rotary shaft therein;

the driving switch installed at a power input end of the driving unit to switch on/off a power supply of the driving unit; and a controller controlling the switching on/off of the driving switch to control operating state of the driving unit and vibration state of the vibrator according to the operation of the driving unit.

3. The massage device for face as claimed in claim 2, wherein the controller controls the driving switch to switch on/off by a preset time interval in pulse width modulation (PWM).

4. The massage device for face as claimed in claim 1, further comprising a wearing unit enabling a user to wear the mask on his/her head.

\* \* \* \* \*